(12) United States Patent
Darby, II et al.

(10) Patent No.: US 8,201,346 B2
(45) Date of Patent: Jun. 19, 2012

(54) MEDICAL SHOE SYSTEM

(75) Inventors: H. Darrel Darby, II, Huntington, WV (US); Wu Zhang, Proctorville, OH (US)

(73) Assignee: Darco International, Inc., Huntington, WV (US)

( * ) Notice: Subject to any disclaimer, the term of this patent is extended or adjusted under 35 U.S.C. 154(b) by 962 days.

(21) Appl. No.: 12/164,430

(22) Filed: Jun. 30, 2008

(65) Prior Publication Data

US 2009/0320329 A1    Dec. 31, 2009

(51) Int. Cl.
*A43B 13/42* (2006.01)
*A43B 13/38* (2006.01)
*A43C 11/00* (2006.01)

(52) U.S. Cl. .............. 36/76 R; 36/110; 36/50.1; 36/44; 36/100

(58) Field of Classification Search .................. 36/76 R, 36/110, 50.1, 44, 100, 43, 30 R, 76 C
See application file for complete search history.

(56) References Cited

U.S. PATENT DOCUMENTS

| | | | | |
|---|---|---|---|---|
| 874,396 A * | 12/1907 | Delbon | ......................... | 36/76 R |
| 1,711,788 A * | 5/1929 | Incutti | ............................ | 36/76 R |
| 3,584,402 A * | 6/1971 | Silverman | ...................... | 36/11.5 |
| 4,103,440 A * | 8/1978 | Lawrence | ........................ | 36/101 |
| 5,329,705 A * | 7/1994 | Grim et al. | ........................ | 36/88 |
| 5,452,526 A * | 9/1995 | Collins | ........................ | 36/76 R |
| 5,483,757 A * | 1/1996 | Frykberg | ......................... | 36/101 |
| 5,491,909 A * | 2/1996 | Darby | ............................. | 36/28 |
| 5,768,803 A * | 6/1998 | Levy | .................................... | 36/43 |
| 5,940,992 A * | 8/1999 | Darby | ............................ | 36/110 |
| 6,061,929 A * | 5/2000 | Ritter | ............................... | 36/107 |
| 6,508,017 B1 * | 1/2003 | DeBarro et al. | .................. | 36/28 |
| 6,792,699 B2 * | 9/2004 | Long et al. | ........................ | 36/88 |
| 6,796,058 B2 * | 9/2004 | Pochatko | ......................... | 36/102 |
| 7,231,728 B2 * | 6/2007 | Darby | ............................. | 36/110 |
| 7,565,754 B1 * | 7/2009 | Acheson et al. | .................. | 36/28 |

* cited by examiner

*Primary Examiner* — Ted Kavanaugh
(74) *Attorney, Agent, or Firm* — Sughrue Mion, PLLC

(57) ABSTRACT

A system, method, and apparatus for treating a foot using a medical shoe and interchangeable insoles. A plurality of interchangeable insoles is provided, including a surgical insole and a wound care insole. The surgical insole provides rigidity for a patient's foot. The surgical insole comprises a first upper layer and a rigid second lower layer. The wound care insole offloads weight from a wound region on the foot. The wound care insole comprises a first upper layer of stretchy, thin film, a second, middle, layer that is moldable, and a third, lower layer that is spongy and provides support.

20 Claims, 14 Drawing Sheets

MEDICAL SHOE SYSTEM

BACKGROUND OF THE INVENTION

1. Field of the Invention

Systems and methods consistent with the invention relate to treating a foot with a medical shoe.

2. Description of the Related Art

Podiatric specialists and other medical professionals providing podiatric treatment and surgery often use medical shoes in the course of therapy. Certain medical shoes may be used to provide support and rigidity after podiatric surgery. Other medical shoes may be used to offload weight from a wound or other sensitive area on the foot. Still other shoes are used to accommodate and protect casts that may be applied to the foot and lower leg after surgery or trauma.

Podiatric specialists and other medical professionals providing podiatric treatment select a medical shoe to be used as part of a treatment regimen based on the specific problem to be solved and the particular characteristics of a patient's foot. For example, one type of medical shoe is used to provide rigidity after surgery, another type of medical shoe is used to offload weight from a wound or other sensitive area, and yet another type of medical shoe is used to accommodate and protect lower leg casts.

Thus, it is necessary for podiatric specialists and other medical professionals providing podiatric treatment to have available a wide variety of medical shoes in their offices or other treatment facilities in order to ensure that the proper medical shoe is available for each patient requiring the use of a medical shoe. This wide variety of medical shoes takes up a significant amount of space in providers' offices or treatment facilities and dramatically increases the amount of inventory needed to provide a wide range of treatment options.

SUMMARY OF THE INVENTION

Exemplary embodiments of the present invention may overcome the above disadvantages and other disadvantages not described above. The present invention is not necessarily required to overcome at least some of the disadvantages described above, and the exemplary embodiments of the present invention may not overcome at least some of the problems described above. The appended claims should be consulted to ascertain the true scope of the invention.

Exemplary embodiments of the present invention relate to a medical shoe and a system and method for treating a foot.

According to an exemplary embodiment of the present invention, a method for treating a foot is provided. The method includes providing a shoe including a circumferential hollow; and providing a plurality of interchangeable insoles for the shoe; wherein the plurality of interchangeable insoles for the shoe includes a wound care insole and a surgical insole; and wherein substantially a circumference of the wound care insole contacts walls of the circumferential hollow when the wound care insole is provided in the shoe, and substantially a circumference of the surgical insole contacts the walls of the circumferential hollow when the surgical insole is provided in the shoe.

According to another exemplary embodiment of the present invention, a system for treating a foot is provided. The system includes a shoe including a circumferential hollow; and a plurality of interchangeable insoles for the shoe; wherein the plurality of interchangeable insoles for the shoe includes a wound care insole, and a surgical insole; and wherein substantially a circumference of the of the wound care insole contacts walls of the circumferential hollow when the wound care insole is provided in the shoe, and substantially a circumference of the surgical insole contacts the walls of the circumferential hollow when the surgical insole is provided in the shoe.

BRIEF DESCRIPTION OF THE DRAWINGS

The above and other aspects of the present invention will become more apparent by describing in detail exemplary embodiments thereof with reference to the attached drawings in which.

DETAILED DESCRIPTION OF THE INVENTION

Figure 1A:
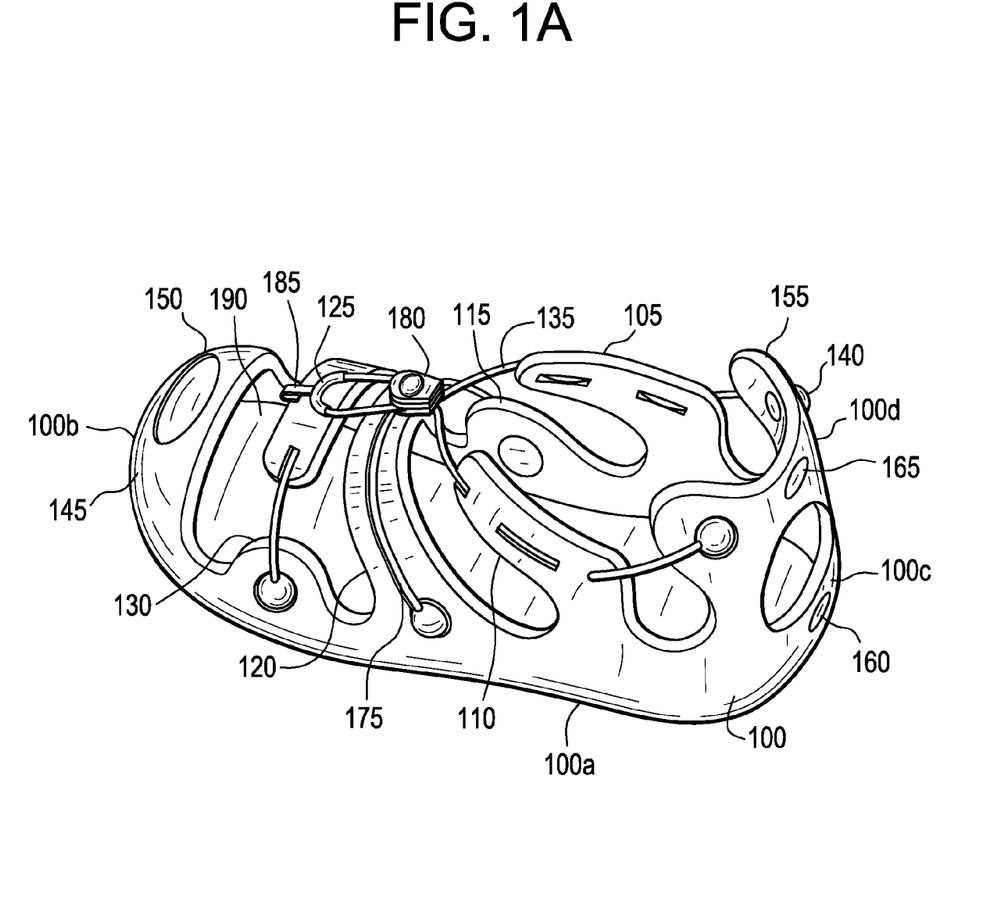
FIG. 1A shows a left side angled view of a medical shoe in accordance with an exemplary embodiment of the present invention.
Figure 1B:
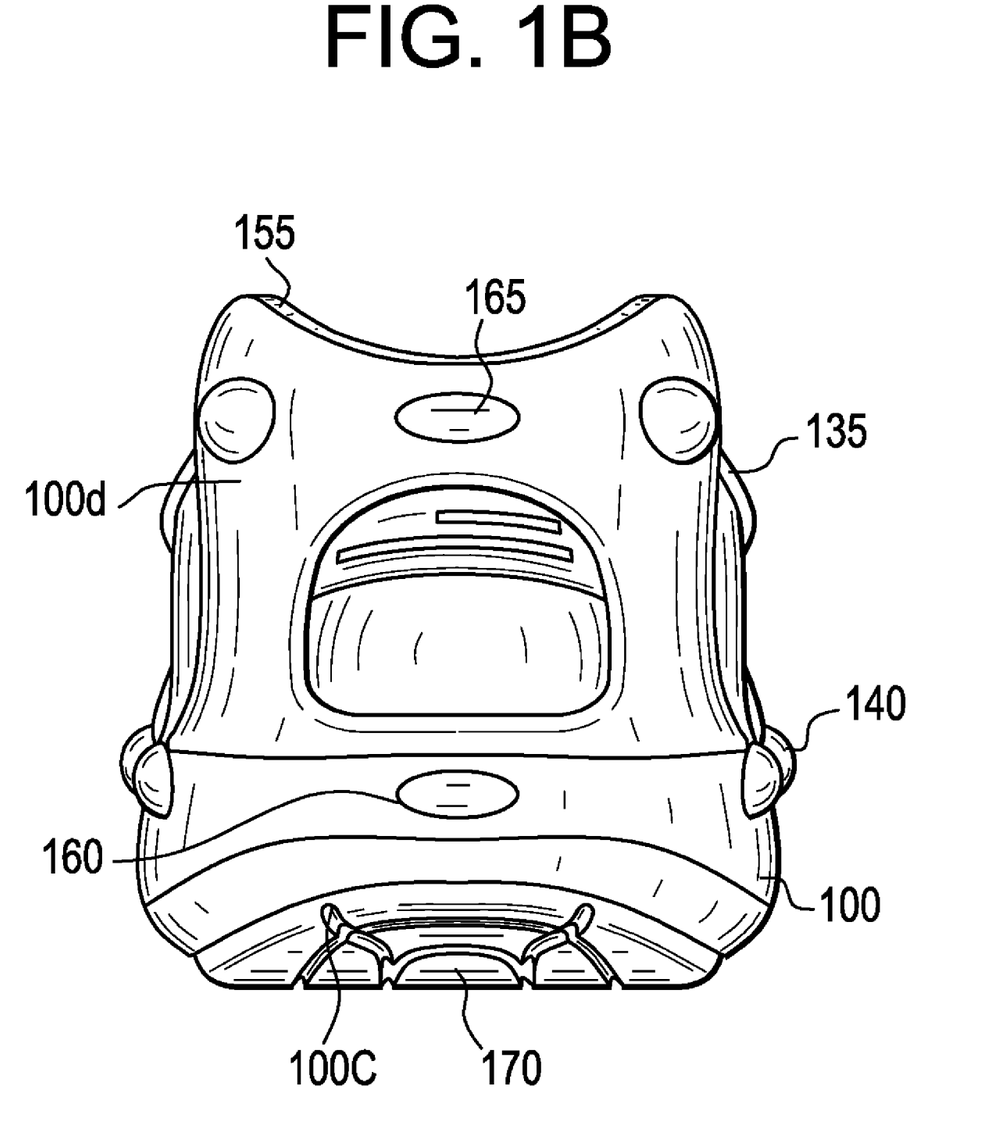
FIG. 1B shows a rear view of the medical shoe in accordance with an exemplary embodiment of the present invention.

According to an exemplary embodiment of the present invention, a medical shoe and a system and method for treating a foot using a medical shoe are provided. FIG. 1A shows a left side angled view of a medical shoe 100 in accordance with an exemplary embodiment of the present invention. FIG. 1B shows a rear view of the medical shoe 100 in accordance with an exemplary embodiment of the present invention. FIG.

Figure 1C:
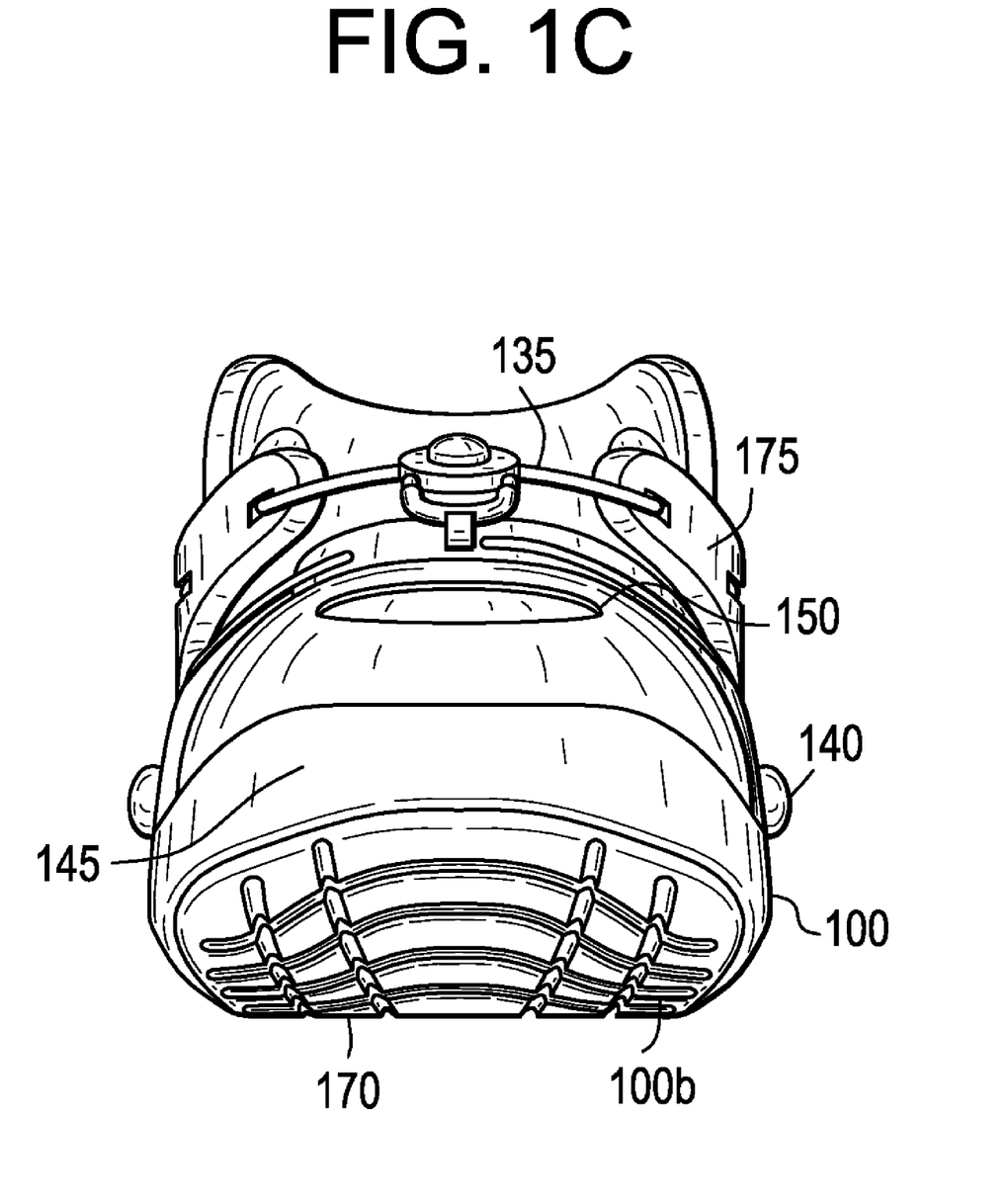
FIG. 1C shows a front view of the medical shoe in accordance with an exemplary embodiment of the present invention.

1C shows a front view of the medical shoe 100 in accordance with an exemplary embodiment of the present invention.

According to an exemplary embodiment, the medical shoe 100 comprises a plurality of projections 105, 110, 115, 120, 125, and 130 extending upward from a lower part of the medical shoe 100. Two symmetrical projections 105 and 110 are provided at the rear of the shoe, and two pairs of asymmetrical projections 115 and 120, and 125 and 130 are provided forward of the symmetrical projections 105 and 110. The medical shoe 100 is designed to so that it can be worn on either the patient's left foot or the patient's right foot. Accordingly, the overall shape of the upper portion of the medical shoe 100 is symmetrical.

The first pair of asymmetrical projections 115 and 120, located forward with respect to the symmetrical projections 105 and 110, is provided so that the projection 120 on the medial side extends past a midway plane of the medical shoe 100 and is longer then the projection 115 on the lateral side. A second pair of asymmetrical projections 125 and 130, located forward with respect to the first pair of asymmetrical projections 115 and 120, is provided so that the projection 125 on the lateral side extends past a midway plane of the medical shoe 100 and is longer than the projection 130 on the medial side. Some of these projections 105, 110, 115, 120, 125, and 130 include channels or grooves 175 that hold elastic strings or wires 135. According to an exemplary embodiment, these projections 105, 110, 115, 120, 125, and 130 may serve to protect the foot and secure the foot in the medical shoe 100.

In addition to these projections 105, 110, 115, 120, 125, and 130, the medical shoe 100 comprises a plurality of buttons 140, within which end knots of the elastic strings or wires 135 are provided. These buttons 140 hold the ends of the elastic strings or wires 135 in place. In another exemplary embodiment of the invention, described below, clasps may be provided in place of at least one of the buttons 140.

According to an exemplary embodiment, a wire 135 extends from a button 140 on an ankle portion 100d of the medical shoe 100, through a channel 175 on a first rear projection 105, through fastener pieces 180 and 185, through a channel 175 on a second rear projection 110, to another button 140 on the ankle portion 100d of the medical shoe 100. Another wire 135 extends from a button 140 on the longer projection 120 of the first pair of asymmetrical projections 115 and 120, through a channel 175 on the longer projection 120 of the first pair of asymmetrical projections 115 and 120, through a channel 175 on the shorter projection 115 of the first pair of asymmetrical projections 115 and 120, to a button 140 on the shorter projection 115 of the first pair of asymmetrical projections 115 and 120. Yet another wire 135 extends from a button 140 on the shorter projection 130 of the second pair of asymmetrical projections 125 and 130, through a channel 175 on the shorter projection 130 of the second pair of asymmetrical projections 125 and 130, through a channel 175 on the longer projection 125 of the second pair of asymmetrical projections 125 and 130, to a button 140 on the longer projection 125 of the second pair of asymmetrical projections 125 and 130.

Also, according to an exemplary embodiment, the medical shoe 100 includes a toe cap 145 with an oval indentation 150. The front of the toe cap 145 is relatively flat.

The back 155 of the medical shoe 100 provides support behind the patient's ankle. Two oval shaped logos 160 and 165 are included in the center of the heel 100c and ankle portions 100d.

According to an exemplary embodiment of the invention, the bottom 100a of the medical shoe 100 is generally flat although it curves upward at the front of the medical shoe 100 near the toe area 100b and it curves upward slightly at the rear of the medical shoe 100 near the heel area 100c. The bottom 100a of the medical shoe 100 has a tread pattern 170. Also, the tread pattern 170 is flat and does not extend up the side of the medical shoe 100.

The body of the medical shoe 100 is thermoplastic urethane (hereinafter "TPU") or an Ethyl Vinyl Acetate (hereinafter "EVA") material according to an exemplary embodiment of the present invention.

According to an exemplary embodiment, the lower part of the medical shoe 100 comprises a circumferential hollow 190 that secures different insoles or sets of insoles. Specifically, the same medical shoe 100 can secure either a removable surgical insole or a removable wound care insole. Substantially a circumference of the of the wound care insole contacts the circumferential hollow when the wound care insole is provided in the shoe, and substantially a circumference of the surgical insole contacts the circumferential hollow when the surgical insole is provided in the shoe.

The medical shoe 100 is shown in FIG. 1A without an insole. In cases where the patient is fitted with a cast, no insole is used. The space that the insole would normally take up, for example, the circumferential hollow 190, is used to accommodate the bulkier size of the cast.

Figure 2A:
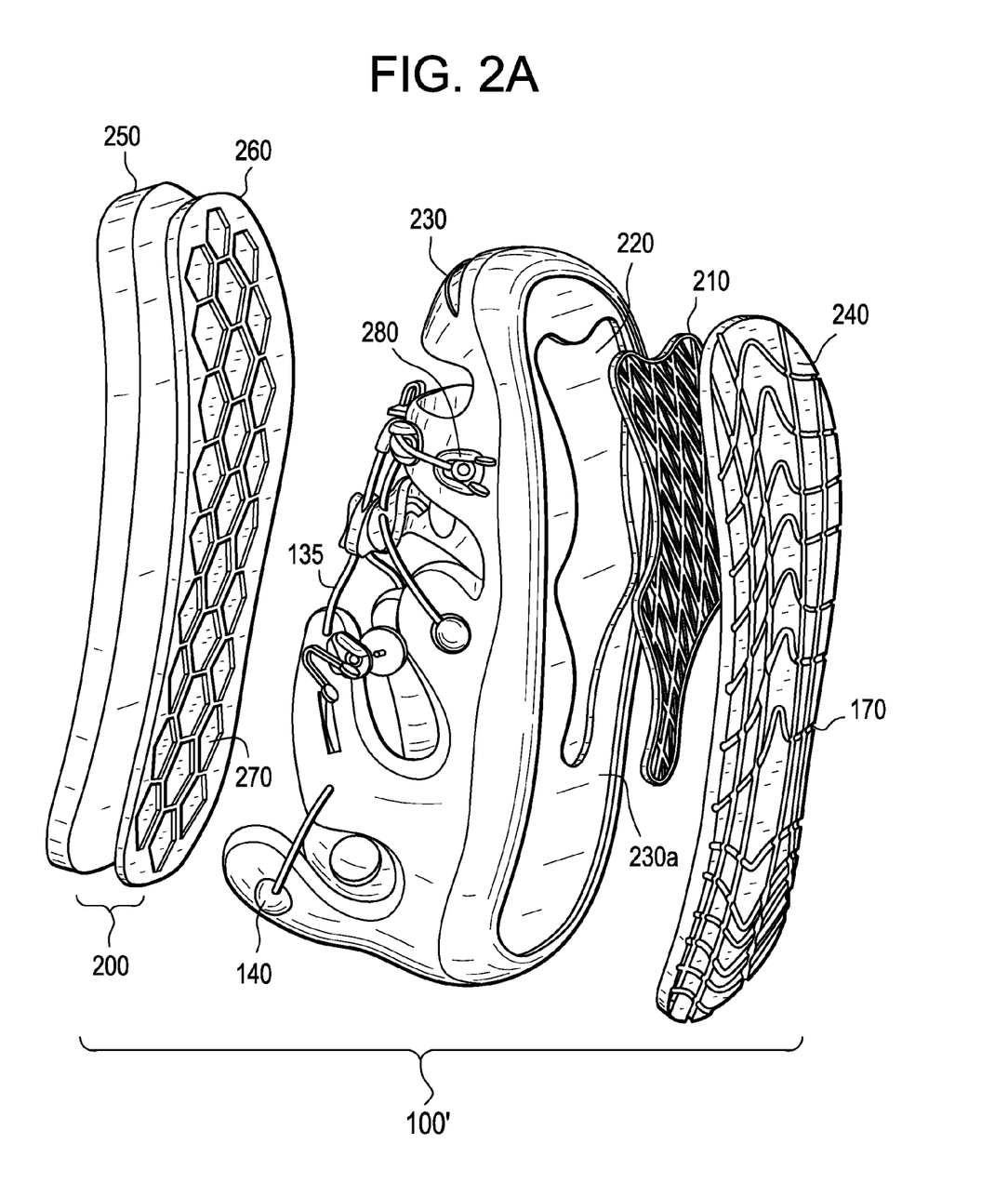
FIG. 2A shows an exploded three-dimensional view of a medical shoe with a removable surgical insole in accordance with another exemplary embodiment of the present invention.
Figure 2B:
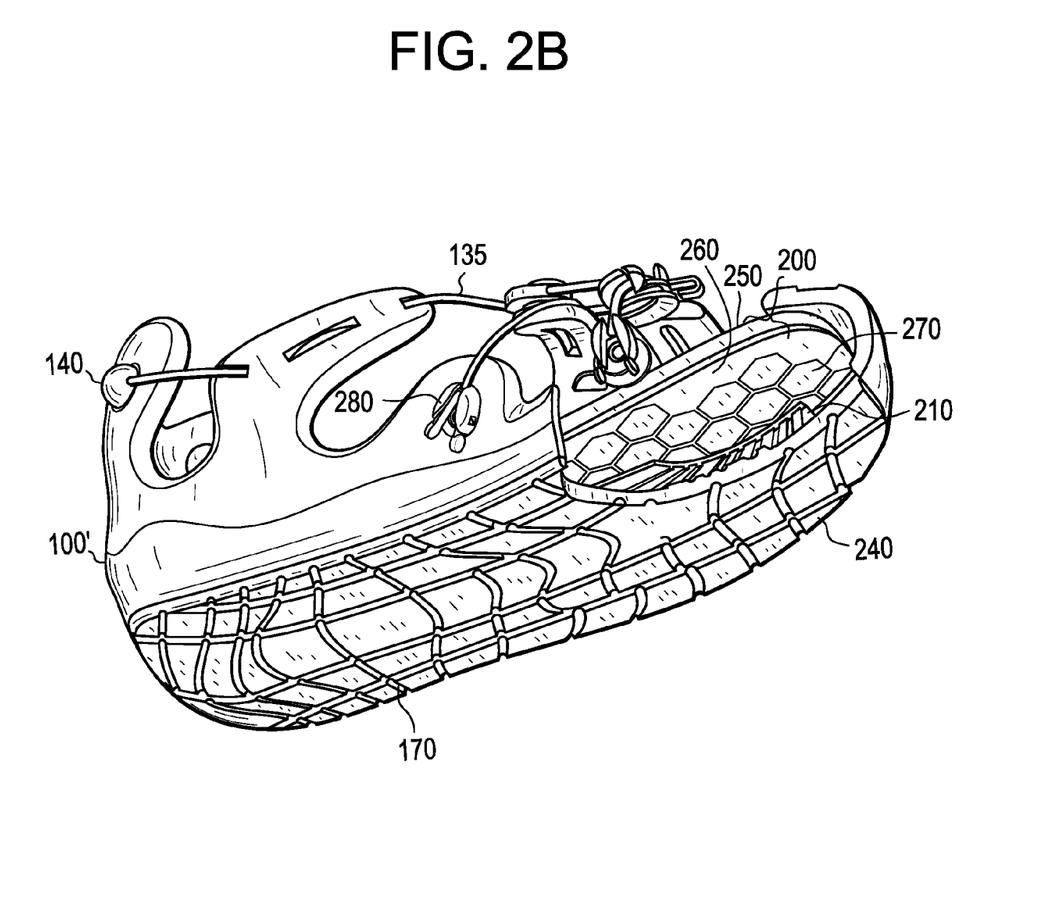
FIG. 2B shows a three-dimensional cutaway view of the medical shoe with the removable surgical insole in accordance with an exemplary embodiment of the present invention.

FIG. 2A shows an exploded three-dimensional view of a medical shoe 100' with a removable surgical insole 200 in accordance with another exemplary embodiment of the present invention. FIG. 2B shows a three-dimensional cutaway view of the medical shoe 100' with the removable surgical insole 200 in accordance with an exemplary embodiment of the present invention. The removable surgical insole 200 is placed within the hollow 190 of the medical shoe 100'.

The embodiment of the medical shoe 100' shown in FIGS. 2A and 2B can accommodate a plurality of insoles, including both the removable surgical insole 200 and the removable wound care insole. Likewise, the embodiment of the medical shoe 100 shown in FIGS. 1A, 1B, and 1C and in FIGS. 4A and 4B can accommodate a plurality of insoles, including both the removable surgical insole 200 and the removable wound care insole.

According to an exemplary embodiment of the invention, the medical shoe 100' comprises a rigid shank 210 that provides support at the bottom portion 230a of the body 230 of the medical shoe 100'. The rigid shank 210 may be made of ABS, nylon, or PVC. The rigid shank 210 fits in an indentation 220 formed in the bottom portion 230a of the body 230 of the medical shoe 100'.

A rigid plate 240 forms the bottom surface of the medical shoe 100' and according to an exemplary embodiment is ABS, nylon, or another hard plastic. The same rigid plate 240 is directly adjacent to the bottom surface of the rigid shank 210 and directly adjacent to the bottom portion 230a of the body 230 of the medical shoe 100' in the regions beyond the edges of the rigid shank 210. The rigid plate 240 has a tread pattern 170 comprising channels or grooves.

In this embodiment, a clasp 280 is provided in conjunction with elastic strings or wires 135 and buttons 140 to permit the adjustment of the medical shoe 100' to fit various size feet and to allow a patient to place his or her foot within the projections of the medical shoe 100'.

The removable surgical insole 200 is adjacent to the top side of the bottom portion 230a of the body 230 of the medical shoe 100'. The removable surgical insole 200 is comprised of an upper portion 250 that according to an exemplary embodiment is made of EVA and a lower portion 260 that according to an exemplary embodiment is rigid and made of ABS, nylon, or another hard plastic. According to an exemplary embodiment, the bottom of the lower portion 260 of the removable surgical insole 200 has a hexagonal pattern 270.

Figure 3:
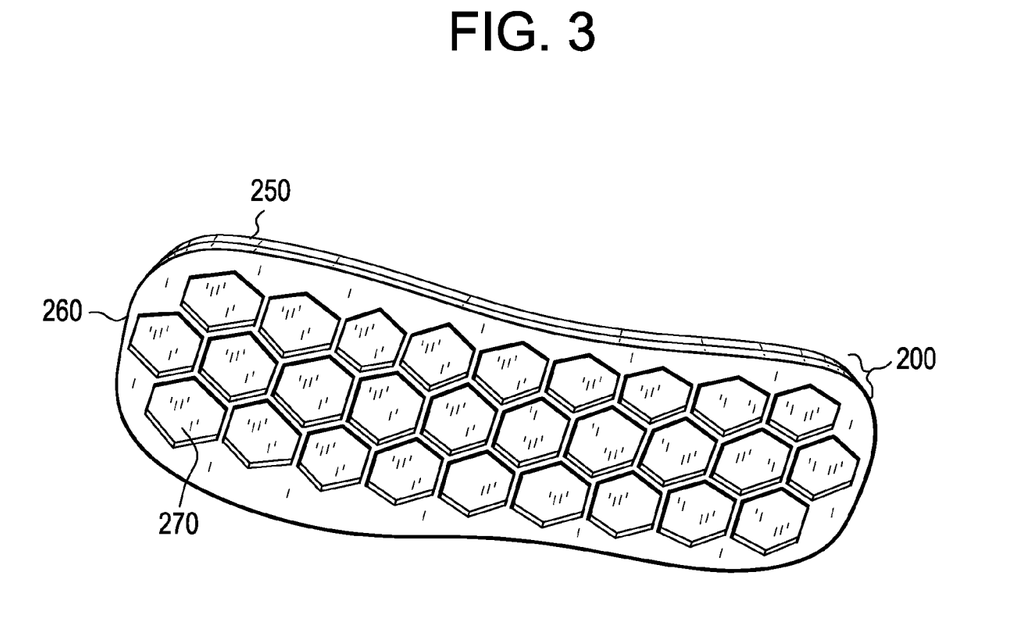
FIG. 3 shows an angled view of the removable surgical insole in accordance with an exemplary embodiment of the present invention.

FIG. 3 shows an angled view of the removable surgical insole 200 in accordance with an exemplary embodiment of the present invention.

Figure 4A:
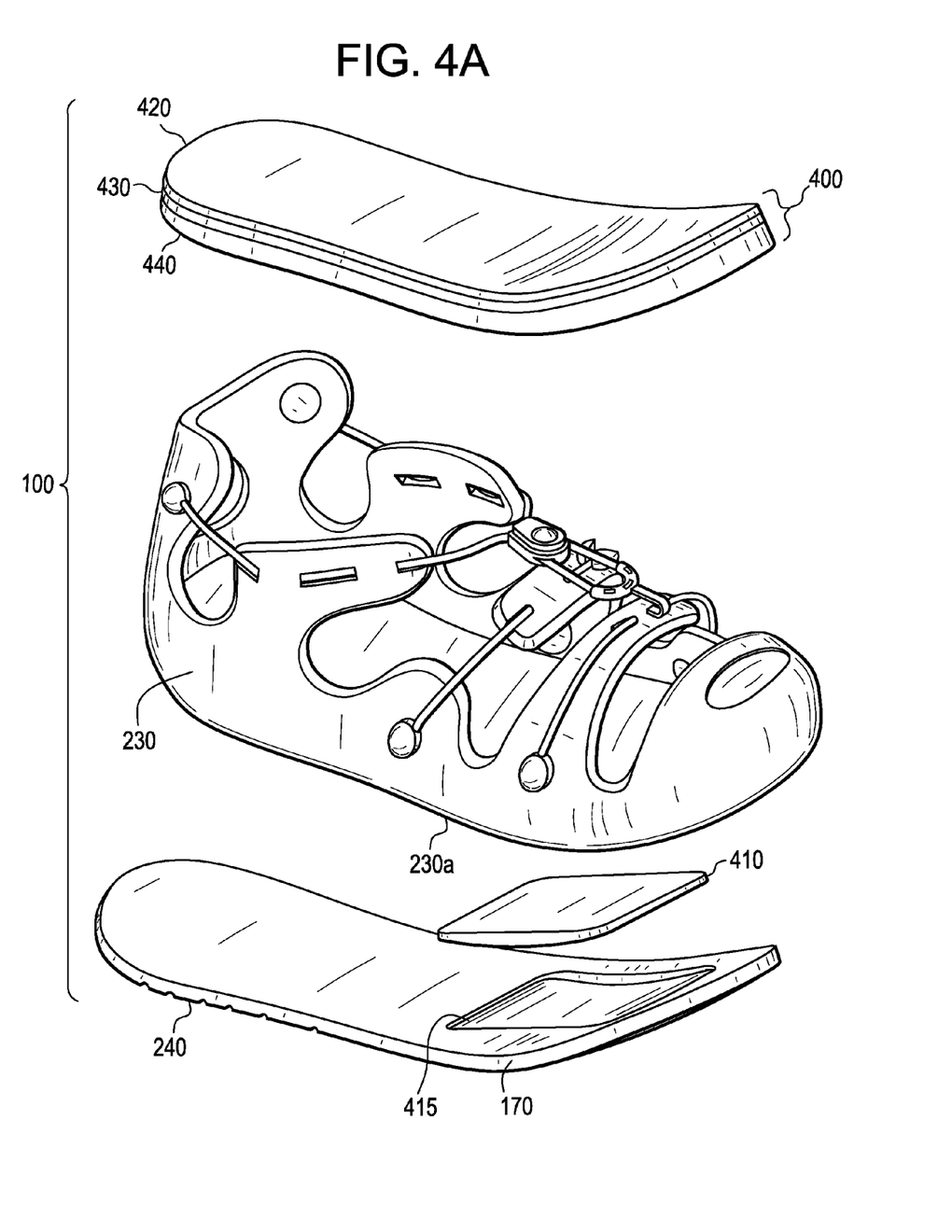
FIG. 4A shows an exploded three-dimensional view of the medical shoe with a removable wound care insole in accordance with an exemplary embodiment of the present invention.
Figure 4B:
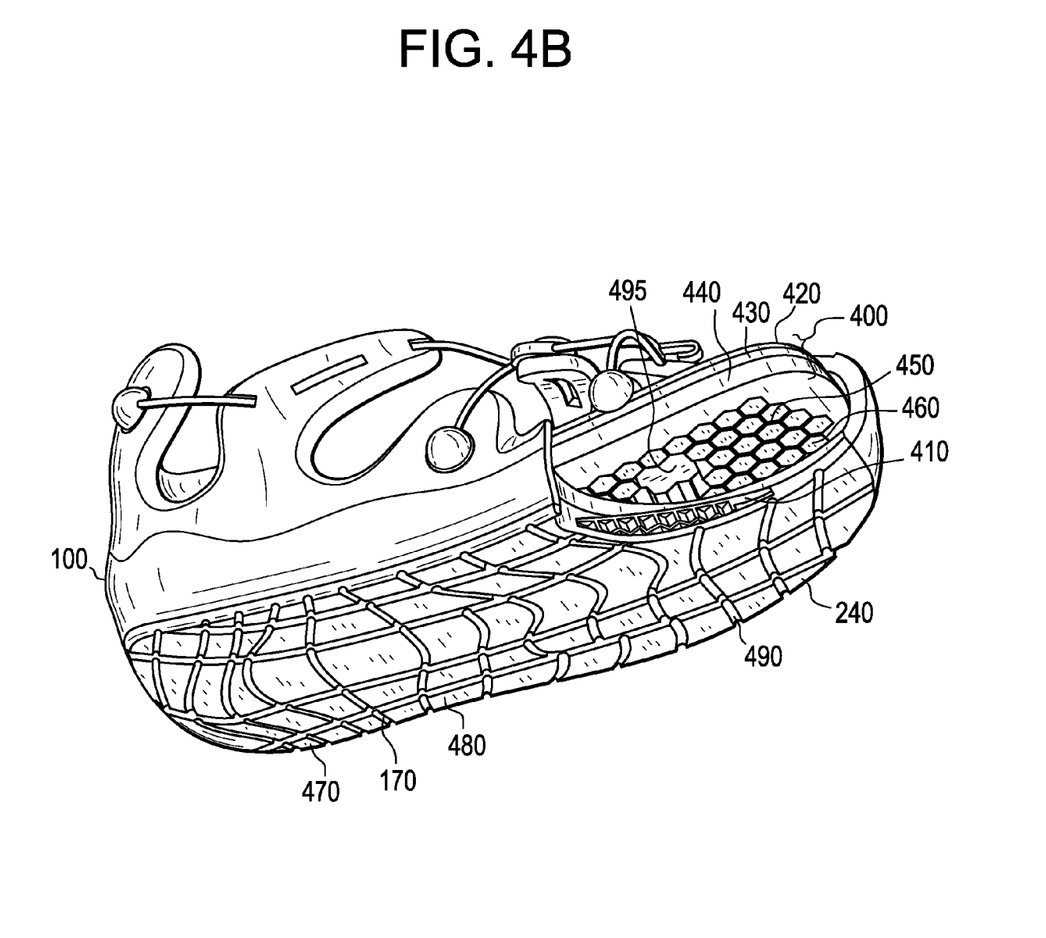
FIG. 4B shows a three-dimensional cutaway view of the medical shoe with the removable wound care insole in accordance with an exemplary embodiment of the present invention.

FIG. 4A shows an exploded three-dimensional view of the medical shoe 100 with a removable wound care insole 400 in accordance with an exemplary embodiment of the present invention. FIG. 4B shows a three-dimensional cutaway view of the medical shoe 100 with the removable wound care insole 400 in accordance with an exemplary embodiment of the present invention.

According to this embodiment, the medical shoe 100 comprises a rigid shank 410 that provides support at the bottom portion 230a of the body 230 of the medical shoe 100, however the rigid shank 210 could also be used. The rigid shank 410 may be made of ABS, nylon, or PVC. The rigid shank 410 fits in an indentation 415 formed on the upper side of a rigid plate 240.

The same rigid plate 240 forms the bottom surface of the medical shoe 100 and according to an exemplary embodiment is ABS, nylon, or another hard plastic. The rigid plate 240 is directly adjacent to the bottom surface of the rigid shank 410 and directly adjacent to the bottom portion 230a of the body 230 of the medical shoe 100 in the regions beyond the edges of the rigid shank 410. The rigid plate 240 has a tread pattern 170 comprising channels or grooves.

The removable wound care insole 400 is adjacent to the top side of the bottom portion 230a of the body 230 of the medical shoe 100. The removable wound care insole 400 comprises an upper portion 420 that according to an exemplary embodiment is a thin, stretchy film such as Poron®. The removable wound care insole 400 further comprises the middle portion 430 that in an exemplary embodiment of the invention is a moldable Plastazote material. The removable wound care insole 400 still further comprises the lower portion 440 that in an exemplary embodiment is made of EVA. The lower portion 440 of the removable wound care insole 400 is spongy and provides support. According to an exemplary embodiment, the removable wound care insole 400 is thicker than the removable surgical insole 200.

The middle portion 430 of the removable wound care insole 400 and the lower portion 440 of the removable wound care insole 400 are perforated by a plurality of perforations 450, each of the plurality of perforations 450 making possible removal of peg shaped portions 460 of the middle portion 430 of the removable wound care insole 400 and the lower portion 440 of the removable wound care insole 400. According to an exemplary embodiment, the perforations 450 are arranged to form a pattern comprising a plurality of hexagonal shapes and are arranged in a first heel region 470 and a second region 480 forward of an arch region 490.

Figure 5A:
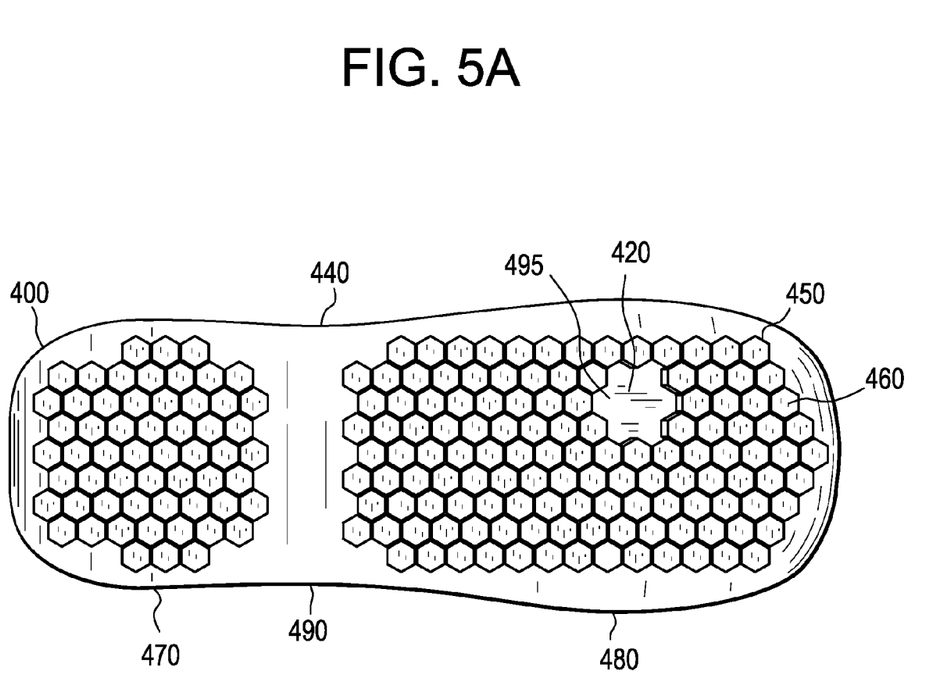
FIG. 5A shows a bottom view of the removable wound care insole in accordance with an exemplary embodiment of the present invention.
Figure 5B:
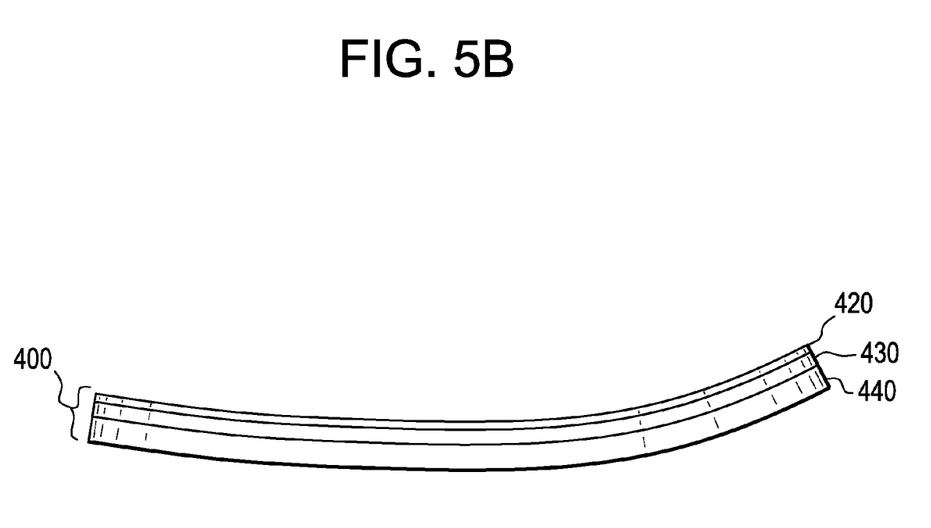
FIG. 5B shows a right side view of the removable wound care insole in accordance with an exemplary embodiment of the present invention.

FIG. 5A shows a bottom view of the removable wound care insole 400 in accordance with an exemplary embodiment of the present invention. FIG. 5B shows a right side view of the removable wound care insole 400 in accordance with an exemplary embodiment of the present invention. One or more of the peg shaped portions 460 of the middle portion 430 and lower portion 440 of the removable wound care insole 400 created by the plurality of perforations 450 may be removed to form an offload region 495 that allows weight to be offloaded from the wound. The offload region 495 has an upper portion 420 but not a middle portion 430 or a lower portion 440.

Figure 6A:
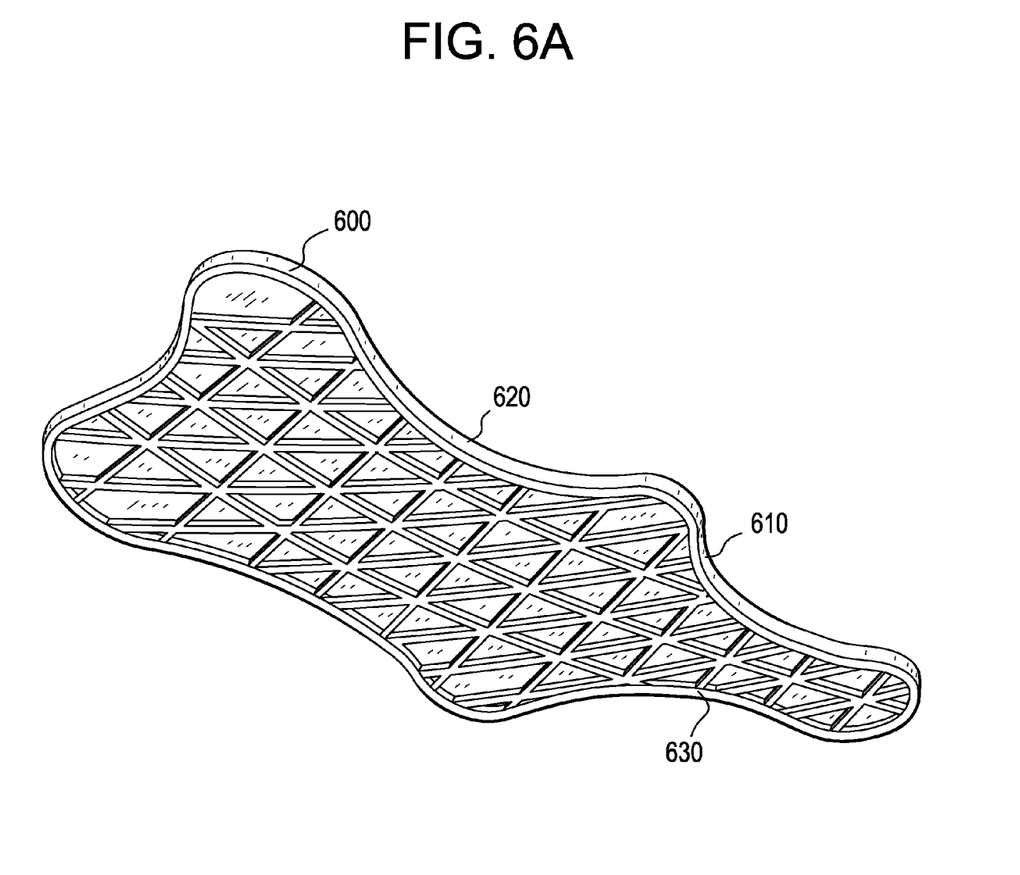
FIG. 6A shows a bottom angled view of a shank in accordance with an exemplary embodiment of the present invention.
Figure 6B:
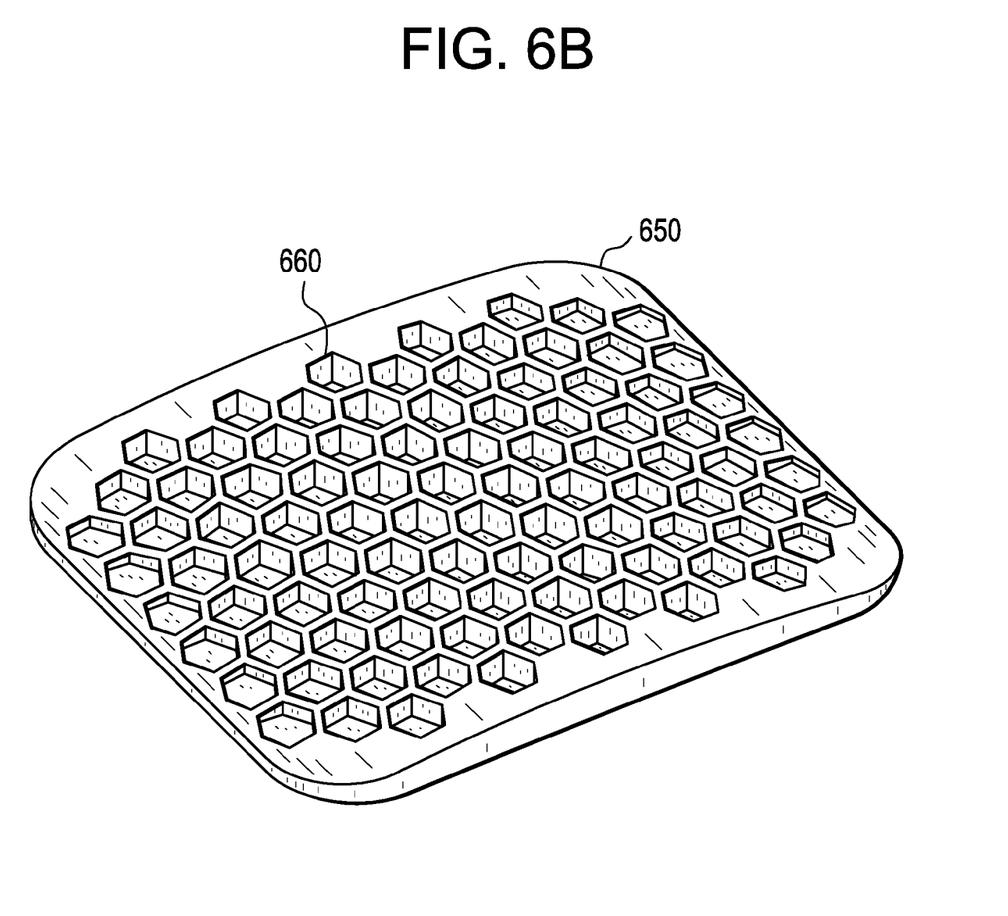
FIG. 6B shows a bottom angled view of a shank in accordance with another exemplary embodiment of the present invention.

FIG. 6A shows a bottom angled view of a shank 600 in accordance with an exemplary embodiment of the present invention. FIG. 6B shows a bottom angled view of a shank 650 in accordance with another exemplary embodiment of the present invention.

FIG. 6A shows a butterfly shaped rigid shank 600 according to an exemplary embodiment of the present invention. The rigid shank 600 may be ABS, nylon, or PVC. The rigid shank 600 has a butterfly shape with a narrow portion in the middle 620 that allows a degree of flexibility in the medical shoe 100' and a triangular pattern 630 that decreases its weight without substantially reducing strength. The rigid shank 600 extends from the portion of the medical shoe 100' adjacent to the forward portion of the foot to the portion of the medical shoe 100' extending past the midfoot (i.e., arch of the foot), in order to provide adequate support.

FIG. 6B shows a rectangular shaped rigid shank 650 according to another exemplary embodiment of the present invention. The rigid shank 650 may be ABS, nylon, or PVC. The rigid shank 650, according to an exemplary embodiment of the invention, has a honeycomb pattern 660 that decreases its weight without substantially reducing strength.

Figure 7:
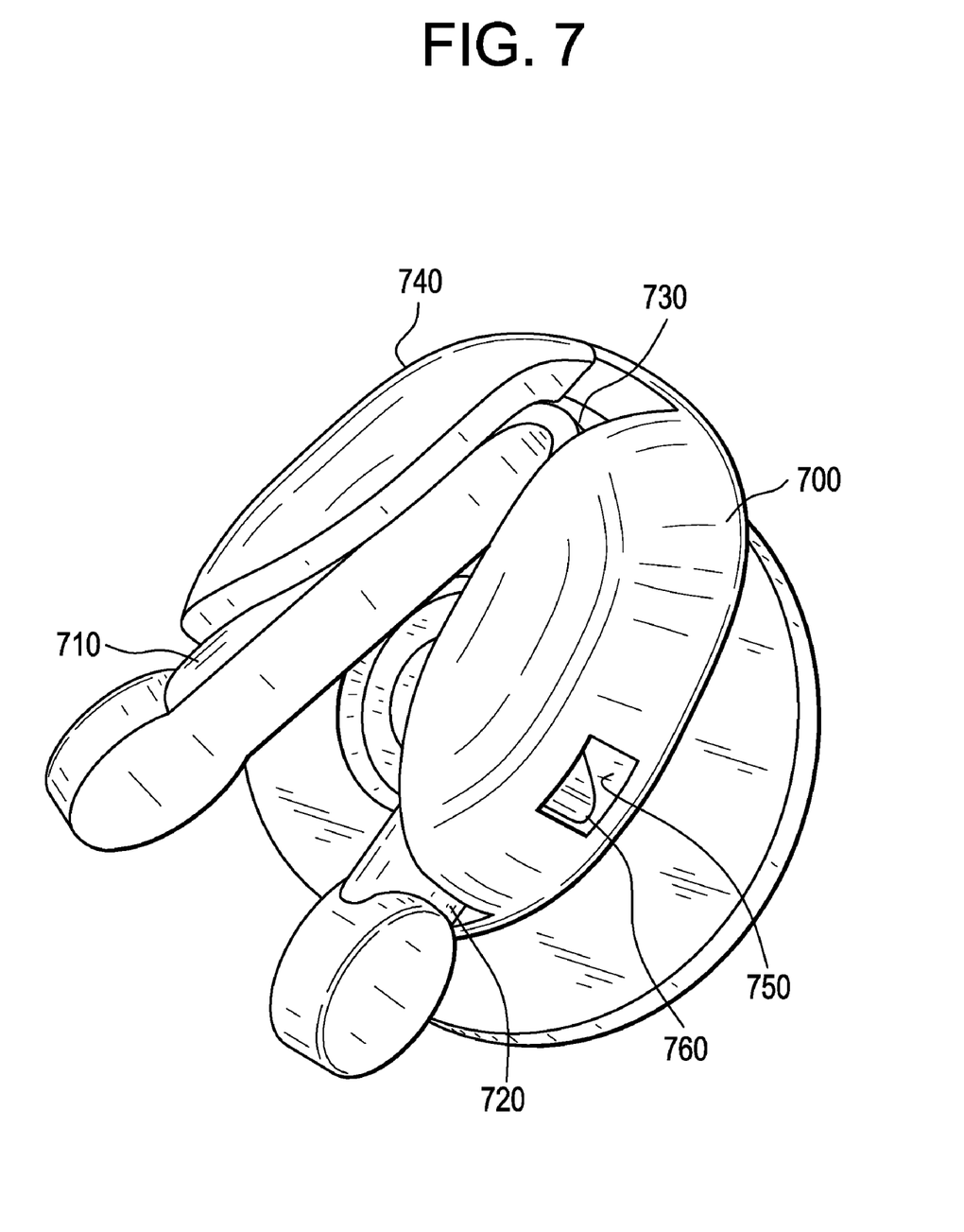
FIG. 7 shows a clasp component of the medical shoe in accordance with an exemplary embodiment of the present invention.

FIG. 7 shows a clasp component 700 of the medical shoe 100' in accordance with an exemplary embodiment of the present invention in a close-up detail view. The clasp 700 is made of ABS, nylon, or another hard plastic, according to an exemplary embodiment of the invention. The clasp 700 has two arms 710 and 720 that are inserted into the body 740 of the clasp 700. A notch 760 on each of on the arms 710 and 720 fits into indentations 750 on the body 740 of the clasp 700 to help hold the arms 710 and 720 in place. There is a hole 730 at the junction of the two arms 710 and 720 permitting the elastic string or wire 135 to pass through.

When the arms 710 and 720 of the clasp 700 are pressed inwardly toward each other, the elastic string or wire 135 may be moved forward or backward through the clasp in order to adjust the fit of the medical shoe 100'. When the arms 710 and 720 of the clasp 700 are released, they return to their original position and the clasp 700 prevents further movement of the elastic string or wire 135. Additionally, the arms 710 and 720 can be removed from the body 740 of the clasp 700. This allows a patient to place his or her foot within the projections of the medical shoe 100'.

According to an exemplary embodiment of the invention, an appropriately sized medical shoe 100' is selected for a patient, along with an interchangeable insole meeting the needs of the prescribed treatment. The selected insole is inserted into the medical shoe 100', and the medical shoe 100' is then fitted to the patient's foot through adjustment of the elastic strings or wires 135 using the clasps 700. In cases where the patient is fitted with a cast, no insole is used. The space that the insole would normally take up is used to accommodate the bulkier size of the cast.

Figure 8:
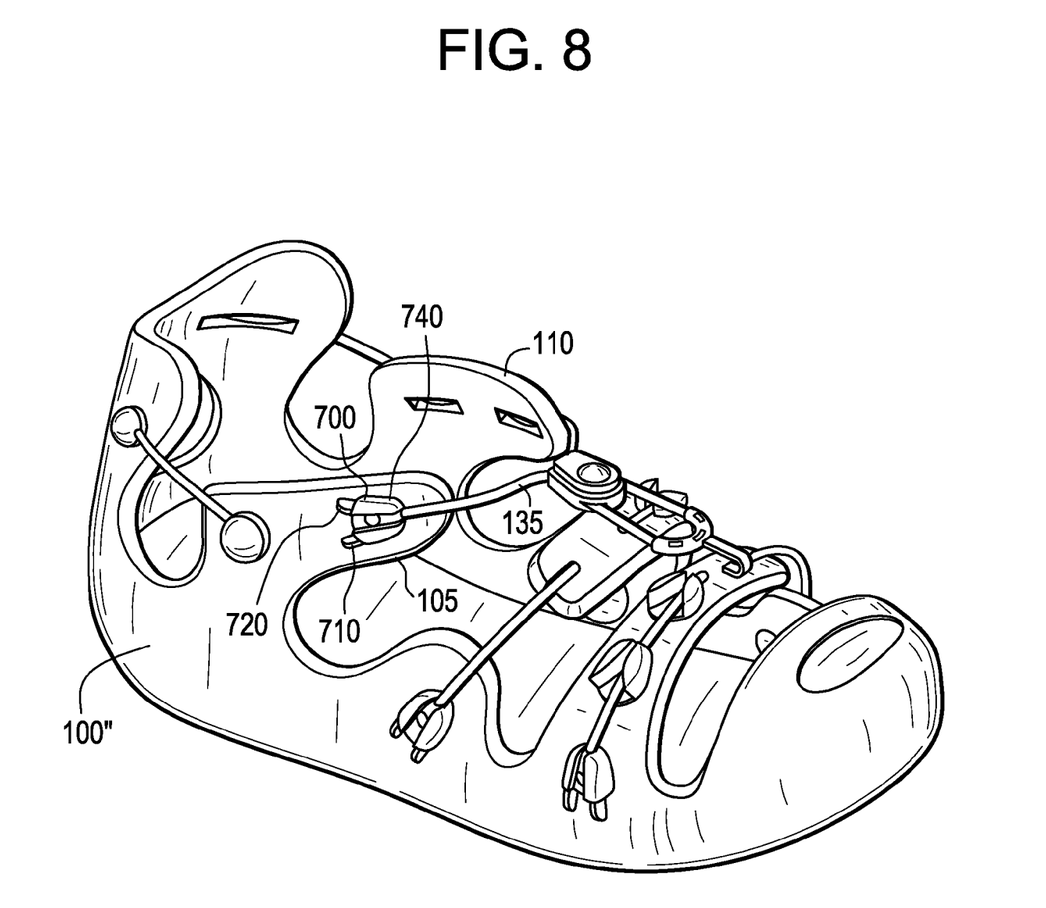
FIG. 8 shows a right side angled view of a medical shoe in accordance with yet another exemplary embodiment of the present invention.

FIG. 8 shows a right side angled view of a medical shoe 100" in accordance with yet another exemplary embodiment of the present invention. According to this embodiment, the arms 710 and 720 can be removed from the body 740 of the clasp 700 located on the projection 105, to permit the string or wire 135 to be moved away from the medical shoe 100" to more easily allow a patient's foot to be dropped into the medical shoe 100".

Additional interchangeable insoles, in addition to the surgical insole 200 and the wound care insole 400, are also contemplated. The invention is not limited to use of the above described insoles.

The invention is not limited to the exemplary embodiments described above. That is, departures can be made from the exemplary embodiment without departing from the spirit and scope of the invention, which is only limited by the following claims.

What is claimed is:

1. A system for treating a foot, comprising:
a shoe including a circumferential hollow; and
a plurality of interchangeable insoles for the shoe;
wherein the plurality of interchangeable insoles for the shoe comprises:
a wound care insole; and
a surgical insole; and
wherein substantially a circumference of the wound care insole contacts walls of the circumferential hollow when the wound care insole is provided in the shoe, and substantially a circumference of the surgical insole contacts the walls of the circumferential hollow when the surgical insole is provided in the shoe,
the shoe further comprising a rigid shank and a rigid plate provided on a bottom portion thereof, the rigid shank being disposed between the bottom portion of the shoe and the rigid plate, such that the rigid plate forms a bottom surface of the shoe.

2. The system of claim 1, wherein the wound care insole comprises:
a plurality of layers; and
a plurality of perforations passing through less than all of the plurality of layers.

3. The system of claim 2, wherein the plurality of perforations are arranged to surround a plurality of portions of the wound care insole, making possible removal of a portion of less than all of the plurality of layers.

4. The system of claim 3, wherein the plurality of portions of the wound care insole surrounded by the plurality of perforations are hexagonal in shape.

5. The system of claim 3, wherein the plurality of portions of the wound care insole surrounded by the plurality of perforations are arranged in a first heel region and a second region forward of an arch region.

6. The system of claim 2,
wherein the plurality of layers comprises:
a first, upper layer;
a second, middle layer; and
a third, lower layer; and
wherein the plurality of perforations pass through the second, middle layer and the third, lower layer but not through the first, upper layer.

7. The system of claim 6,
wherein the first, upper layer is composed of a Poron material;
wherein the second, middle layer is composed of a moldable Plastazote material; and
wherein the third, lower layer is composed of an Ethyl Vinyl Acetate (EVA) material.

8. The system of claim 1, wherein the surgical insole comprises:
a first, upper layer; and
a rigid second, lower layer.

9. The system of claim 8,
wherein the first, upper layer is composed of an Ethyl Vinyl Acetate (EVA) material; and
wherein the second, lower layer is composed of an ABS, nylon, or another hard plastic material.

10. The system of claim 1,
wherein the wound care insole comprises:
a first, upper layer;
a second, middle layer;
a third, lower layer; and
a plurality of perforations passing through less than all of the plurality of layers; and
wherein the surgical insole comprises:
a first, upper layer; and
a rigid second, lower layer.

11. A medical shoe for treating a foot, the medical shoe comprising:
a rigid shank,
wherein the rigid shank comprises:
a first wider portion which is provided at a front of the rigid shank;
a narrow portion;
a second wider portion; and
a neck portion which is provided at a rear of the rigid shank;
wherein the narrow portion is provided between the first wider portion and the second wider portion;
wherein the neck portion is narrower than the first wider portion, the second wider portion, and the narrow portion; and
wherein the rigid shank is disposed between a body of the medical shoe and a rigid plate forming a bottom surface of the medical shoe.

12. The medical shoe of claim 11, wherein the rigid shank includes rounded vertices and curved, concave sides.

13. The medical shoe of claim 11, wherein the neck portion of the rigid shank extends past an arch portion of the foot.

14. The medical shoe of claim 11, wherein the rigid shank is composed of at least one of ABS, nylon, and PVC.

15. The medical shoe of claim 11, wherein the rigid shank further comprises ribs provided at one surface of the rigid shank.

16. The medical shoe of claim 11, wherein the rigid shank further comprises a triangular pattern on at least one surface of the rigid shank.

17. The medical shoe of claim 16, wherein the triangular pattern comprises triangular indentations on the at least one surface of the rigid shank.

18. The medical shoe of claim 11, wherein the rigid shank is provided in a bottom portion of a body of the medical shoe.

19. The medical shoe of claim 11, wherein the rigid shank is disposed in an indentation formed in a bottom portion of the body of the medical shoe.

20. The medical shoe of claim 19, wherein the rigid shank extends from a first region of the medical shoe adjacent to a forward portion of a foot to a second region of the medical shoe extending past an arch portion of the foot.

* * * * *